(12) United States Patent
Morris (10) Patent No.: US 6,973,348 B2
(45) Date of Patent: *Dec. 6, 2005

(54) HEART MONITORS WITH ROBUST INTERVAL MEASUREMENTS

(75) Inventor: Milton M. Morris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/292,415

(22) Filed: Nov. 11, 2002

(65) Prior Publication Data

US 2003/0130705 A1 Jul. 10, 2003

Related U.S. Application Data

(63) Continuation of application No. 09/391,111, filed on Sep. 7, 1999, now Pat. No. 6,480,741.

(51) Int. Cl.[7] .............................................. A61N 1/362
(52) U.S. Cl. ......................................................... 607/9
(58) Field of Search ............................. 607/4, 5, 9, 14, 607/27; 600/510, 515

(56) References Cited

U.S. PATENT DOCUMENTS

| 3,707,959 A | 1/1973 | Wilton-Davies ....... 128/2.06 A |
| 3,768,486 A | 10/1973 | Berkovits et al. ......... 128/419 P |
| 3,952,731 A | 4/1976 | Worstencroft .......... 128/2.06 A |
| 4,250,883 A | 2/1981 | Thompson ............. 128/419 PG |
| 4,276,883 A | 7/1981 | McDonald et al. .... 128/419 PT |
| 4,401,120 A | 8/1983 | Hartlaub et al. ....... 128/419 PT |
| 4,493,325 A | 1/1985 | Hartlaub et al. ...... 128/419 PG |
| 4,515,159 A | 5/1985 | McDonald et al. ... 128/419 PG |
| 4,549,548 A | 10/1985 | Wittkampf et al. ... 128/419 PG |
| 4,561,442 A | 12/1985 | Vollmann et al. ..... 128/419 PG |
| 4,712,554 A | 12/1987 | Garson, Jr. ........... 128/419 PG |
| 4,928,688 A | 5/1990 | Mower ................. 128/419 PG |
| 5,042,480 A | 8/1991 | Hedin et al. .......... 128/419 PG |
| 5,085,215 A | 2/1992 | Nappholz et al. ..... 128/419 PG |
| 5,267,559 A | 12/1993 | Jin et al. ................ 128/419 D |
| 5,271,394 A | 12/1993 | Girodo et al. ................ 607/15 |
| 5,312,445 A | 5/1994 | Nappholz et al. ............... 607/9 |
| 5,330,508 A | 7/1994 | Gunderson .................... 607/14 |

(Continued)

FOREIGN PATENT DOCUMENTS

EP  0879620  11/1998  .......... A61N 1/368

(Continued)

*Primary Examiner*—George R. Evanisko
(74) *Attorney, Agent, or Firm*—Schwegman, Lundberg, Woessner & Kluth, P.A.

(57) ABSTRACT

Thousands of patients prone to irregular and sometimes life threatening heart rhythms have miniature heart-monitoring devices, such as defibrillators and cardioverters, implanted in their chests. These devices detect abnormal heart rhythms and automatically apply electrical therapy to restore normal heart function. Significant parts of these devices include the microprocessor and stored instructions, or algorithms, that govern how the devices interpret and react to electrical signals indicative of normal or abnormal heart rhythms. These algorithms generally use the time intervals between successive heart beats, or cardiac events, as a key factor in therapy decisions. To ensure accuracy of interval measurements, the inventor devised new methods for processing heart electrical signals, some of which ensure accurate interval measurements without unduly delaying therapy decisions or consuming significant battery power. One of these new methods detects an abnormal interval measurement and either disqualifies the abnormal interval from use in making therapy decisions or divides the abnormal interval into two or more other intervals, thereby facilitating identification and treatment of abnormal rhythmic conditions both efficiently and accurately.

10 Claims, 4 Drawing Sheets

U.S. PATENT DOCUMENTS

| | | | |
|---|---|---|---|
| 5,366,486 A | 11/1994 | Zipes et al. | 607/5 |
| 5,454,836 A | 10/1995 | van der Veen et al. | 607/9 |
| 5,514,161 A | 5/1996 | Limousin | 607/9 |
| 5,522,852 A | 6/1996 | White et al. | 607/5 |
| 5,549,649 A | 8/1996 | Florio et al. | 607/15 |
| 5,658,320 A | 8/1997 | Betzold et al. | 607/14 |
| 5,672,170 A | 9/1997 | Cho et al. | 606/12 |
| 5,676,686 A | 10/1997 | Jensen et al. | 607/9 |
| 5,755,739 A | 5/1998 | Sun et al. | 607/14 |
| 5,759,196 A | 6/1998 | Hess et al. | 607/14 |
| 5,788,717 A | 8/1998 | Mann et al. | 607/14 |
| 5,867,386 A | 2/1999 | Hoffberg et al. | 364/188 |
| 5,885,221 A | 3/1999 | Hsu et al. | 600/515 |
| 5,893,882 A | 4/1999 | Peterson et al. | 607/14 |
| 5,951,593 A | 9/1999 | Lu et al. | 607/14 |
| 5,978,704 A | 11/1999 | Ideker et al. | 607/5 |
| 5,991,657 A | 11/1999 | Kim | 607/5 |
| 5,999,850 A | 12/1999 | Dawson et al. | 607/4 |
| 6,061,592 A | 5/2000 | Nigam | 600/518 |
| 6,129,745 A * | 10/2000 | Sun et al. | 607/9 |
| 6,480,741 B1 * | 11/2002 | Morris | 607/27 |

FOREIGN PATENT DOCUMENTS

| | | | |
|---|---|---|---|
| WO | WO-97/39799 | 10/1997 | A61N 1/362 |

* cited by examiner

Fig. 4 ated pages.

HEART MONITORS WITH ROBUST INTERVAL MEASUREMENTS

CROSS-REFERENCE TO RELATED APPLICATION(S)

This application is a continuation of U.S. application Ser. No. 09/391,111, filed on Sep. 7, 1999 now U.S Pat. No. 6,480,741, the specification of which is incorporated by reference herein.

TECHNICAL FIELD

The present invention concerns heart-monitoring devices and methods, particularly implantable defibrillators, pacemakers, and cardioverters, and methods for processing heart-signal data.

BACKGROUND OF THE INVENTION

Since the early 1980s, thousands of patients prone to irregular and sometimes life threatening heart rhythms have had miniature heart-monitoring devices, such as defibrillators, pacemakers, and cardioverters, implanted in their bodies. These devices detect onset of abnormal heart rhythms and automatically apply corrective electrical therapy, specifically one or more bursts of electric current, to their hearts. When the bursts of electric current are properly sized and timed, they restore normal heart function without human intervention, sparing patients considerable discomfort and often saving their lives.

The typical implantable heart-monitoring device includes a set of electrical leads, which extend from a sealed housing through the veinous system into the inner walls of a heart after implantation. Within the housing are a battery for supplying power, a capacitor for delivering bursts of electric current through the leads to the heart, and heart-monitoring circuitry for monitoring the heart and determining not only when and where to apply the current bursts but also their number and magnitude. The monitoring circuitry generally includes a microprocessor and a memory that stores instructions directing the microprocessor to interpret electrical signals that naturally occur in the heart as normal or abnormal rhythms. For abnormal rhythms, the instructions, or more generally signal-processing algorithm, also tell the processor what, if any, electrical therapy should be given to restore normal heart function.

In general, these algorithms use the time intervals between successive heart beats, or cardiac events, as a key determinant of therapy decisions. Thus, mistakes in determining these intervals can ultimately undermine the validity of resultant therapy decisions.

Determining these intervals can be especially problematic in dual-chamber devices, which monitor the beats of two chambers of the heart, the left ventricle and the left atrium. In these devices, there is a significant risk of mistaking a ventricle beat for an atrial beat, and therefore counting too many atrial beats and miscalculating some atrial intervals (the time between atrial beats). Because of this risk, many dual-chamber devices include safeguards to ensure accuracy of atrial interval measurements.

There are three basic approaches to designing these safeguards. The first approach, called cross-chamber blanking, entails using a blanking period to prevent sensing atrial beats within a certain time period after the last ventricular beat. In other words, atrial sensing is temporarily disabled after each ventricular beat to prevent mistaking the ventricular beat for an atrial beat. Blanking, however, forces some devices to overlook any atrial beats that might occur during the blanking period. The second approach, which is corrective rather than preventative, entails looking for certain patterns in atrial and ventricular electrograms (signal charts) to identify a ventricular beat mistaken for an atrial beat. If a mistake is detected, this approach discards a select portion of the atrial electrogram. (See U.S. Pat. No. 5,759,196.) Unfortunately, discarding a portion of the atrial electrogram delays the making of therapy decisions. U.S. Pat. No. 5,755,739 reports a third approach which adaptively filters out parts of an atrial electrogram and uses morphologic techniques to verify accuracy of the filtered atrial electrogram. Unfortunately, this corrective approach requires extensive computations and thus not only delays therapy decisions, but also consumes considerable battery power. Accordingly, there is a need for other methods of ensuring accurate interval measurements.

SUMMARY OF THE INVENTION

To address this and other needs, the inventor has devised new methods for processing heart electrical signals, some of which ensure accurate interval measurements without unduly delaying therapy decisions or consuming significant battery power. One of these new methods identifies, or detects, an abnormal interval measurement and then either disqualifies the abnormal interval from use in making therapy decisions or divides the abnormal interval into two or more other intervals.

More particularly, an exemplary embodiment, or implementation, of this method entails first identifying an abnormal interval which has a predetermined size relative one or more preceding intervals, with each interval representing a time between successive atrial events. The method then determines whether a ventricular event occurred during a specific portion of the abnormal interval. If a ventricular event occurred, the method either disqualifies the abnormal interval from further processing or divides it into two or more new intervals for use in further processing, such as computing an average atrial interval.

Ultimately, this and other methods embodying teachings of the present invention, can be incorporated into medical devices, for example, implantable pacemakers, defibrillators, or cardioverter defibrillators, to identify and treat abnormal rhythmic conditions both efficiently and accurately.

DESCRIPTION OF THE PREFERRED EMBODIMENTS

The following detailed description, which references and incorporates FIGS. 1–4, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
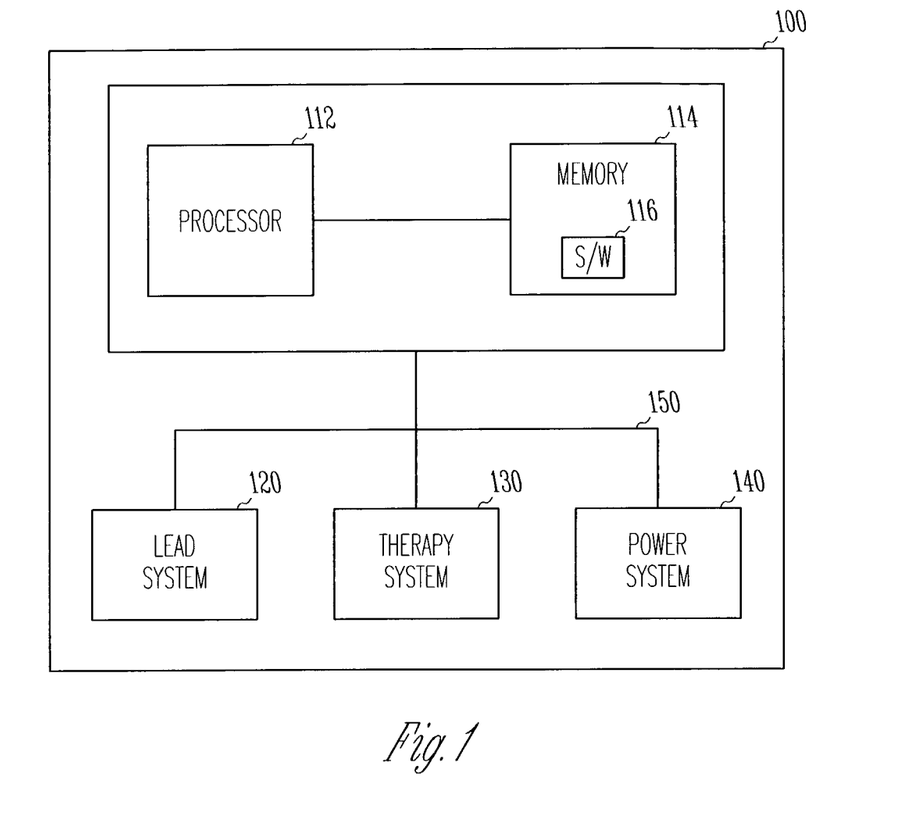
FIG. 1 is a block diagram of an exemplary implantable heart monitor incorporating teachings of the present invention.

FIG. 1 shows an exemplary implantable heart-monitoring device (or pulse generator) 100 incorporating teachings of the present invention. Device 100 includes a monitoring system 110, a lead system 120, a therapy system 130, a power system 140, and an interconnective bus 150. Monitoring system 110 includes a processor or microcontroller 112 and a memory 114. Memory 114 includes one or more software modules 116 which store one or more computer instructions in accord with the present invention. Some embodiments of the invention replace software modules 116 with one or more hardware or firmware modules. In the exemplary embodiment, processor 112 is a ZiLOG™ Z80 microprocessor (with a math coprocessor), and memory 114 is a read-only memory. However, the invention is not limited to any particular microprocessor, microcontroller, or memory.

Lead system 120, in the exemplary embodiment, includes one or more electrically conductive leads—for example, atrial, ventricular, or defibrillation leads—suitable for insertion into a heart. One or more of these are suitable for sensing electrical signals from a portion of the heart and one or more are suitable for transmitting therapeutic doses of electrical energy. Lead system 120 also includes associated sensing and signal-conditioning electronics, such as atrial or ventricular sense amplifiers and/or analog-to-digital converters, as known or will be known in the art.

In some embodiments, lead system 120 supports ventricular epicardial rate sensing, atrial endocardial bipolar pacing and sensing, ventricular endocardial bipolar pacing and sensing, epicardial patches, and Endotak® Series and ancillary leads. In some embodiments, lead system 120 also supports two or more pacing regimens, including DDD pacing. Also, some embodiments use a housing for device 100 as an optional defibrillation electrode. The invention, however, is not limited in terms of lead or electrode types, lead or electrode configurations, sensing electronics, or signal-conditioning electronics.

Therapy system 130 includes one or more capacitors and other circuitry (not shown) for delivering or transmitting electrical energy in measured doses through lead system 120 to a heart or other living tissue. In the exemplary embodiment, therapy system 130 includes aluminum electrolytic or polymer-based capacitors. However, other embodiments use one or more other devices for administering non-electrical therapeutic agents, such as pharmaceuticals, to a heart. Thus, the invention is not limited to any particular type of therapy system.

In general operation, lead system 120 senses atrial or ventricular electrical activity and provides data representative of this activity to monitoring system 110. Monitoring system 110, specifically processor 112, processes this data according to instructions of software module 116 of memory 114. If appropriate, processor 112 then directs or causes therapy system 130 to deliver one or more measured doses of electrical energy or other therapeutic agents through lead system 120 to a heart.

Figure 2:
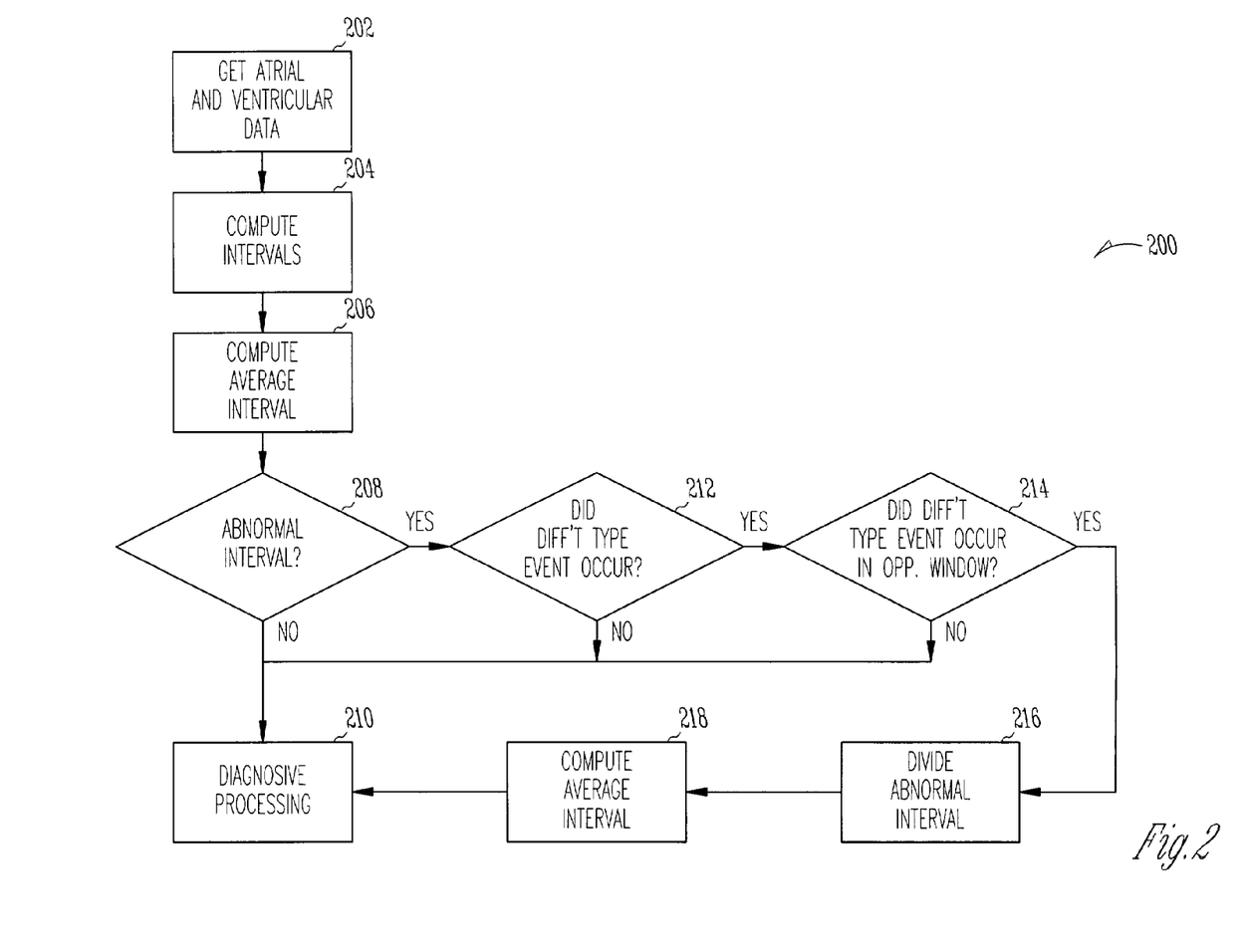
FIG. 2 is a flow chart illustrating an exemplary method incorporating teachings of the present invention.

FIG. 2, which shows an exemplary flow chart 200, illustrates an exemplary data-processing method embodied within software module 116 and executed by processor 112. Flow chart 200 includes blocks 202–220, which are arranged serially in the exemplary embodiment. However, other embodiments of the invention may execute two or more blocks in parallel using multiple processors or a single processor organized as two or more virtual machines or subprocessors. Moreover, still other embodiments implement the blocks as two or more specific interconnected hardware modules with related control and data signals communicated between and through the modules. Thus, the exemplary process flow is instructive to software, firmware, and hardware implementations.

In process block 202, processor 112 of device 100 receives data representative of atrial and ventricular electrical activities. In the exemplary embodiment, this entails receiving data from lead system 120 as digital representations of atrial and ventricular voltage signals. These digital representations are processed and ultimately organized into a data structure bearing information about the temporal relationship of sensed atrial and ventricular events.

Figure 3:
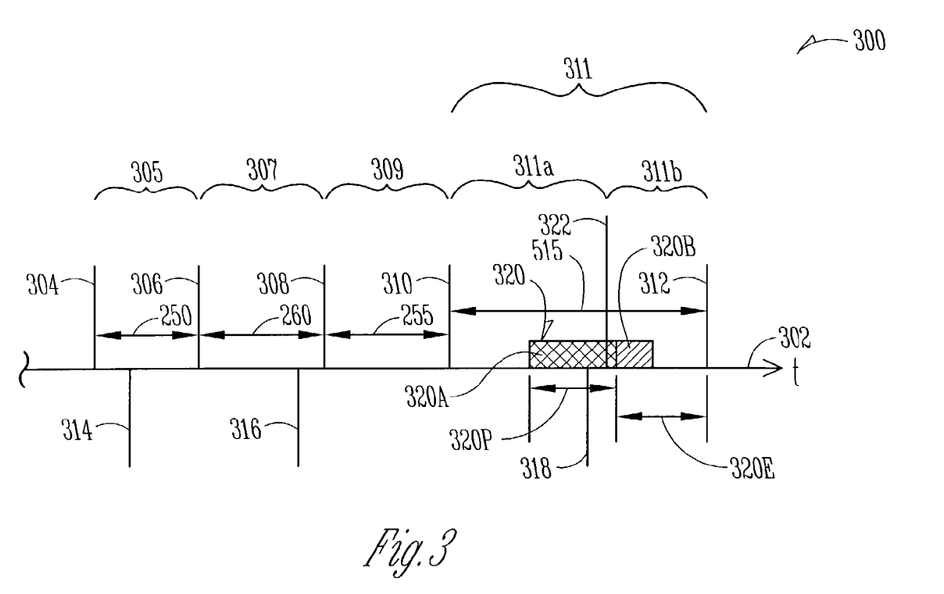
FIG. 3 is an exemplary timing diagram 300 further illustrating teachings of the present invention.

FIG. 3 shows an exemplary timing diagram 300 which aids further description of the exemplary embodiment. Specifically, diagram 300 includes a horizontal time axis 302 and cardiac event markers 304–318. Event markers 304–312, indicative of sensed atrial events, are called atrial event markers, whereas event markers 314–318, which indicate sensed ventricular events, are called ventricular event markers. The time between each consecutive pair of atrial event markers is known as an atrial interval, with the first occurring marker in each pair called a starting, or beginning, marker and the second occurring marker in each pair called a terminal, or end, marker. Atrial event markers 304–312 define four atrial intervals 305, 307, 309, and 311. Atrial event markers 204 and 206 define atrial interval 205; markers 206 and 208 define interval 207; and so forth. Timing diagram 300 also includes a cross-chamber blanking period 320 having a first portion 320a and a second portion 320b.

After receiving and organizing the digital representations of the atrial and ventricular signals into a data structure analogous to FIG. 3, processor 112 executes process block 204 (in FIG. 2). In process block 204, processor 112 calculates a set of Y intervals based on the digital representations of the atrial or ventricular voltage signal. In other words, the processor computes a set of pp-intervals, with each interval based on the time between one depolarization and the next occurring depolarization. Other embodiments compute these intervals based on other generally recurrent features in the electrogram. As FIG. 3 shows, the exemplary embodiment calculates a set of four atrial intervals, such as intervals 305, 307, 309, and 311, which are respectively 250, 260, 255, and 515 milliseconds.

Execution of the exemplary method then continues at process block 206. Block 206 entails calculating a moving average or central tendency of one or more intervals in the set of Y intervals. The exemplary embodiment averages the first three of the four intervals, with each of the first three intervals having an equal weight in the averaging. The average of the first three atrial intervals 305, 307, and 309 in FIG. 3 is 255 milliseconds.

However, other embodiments weight one or more of the intervals differently than others intervals, giving some intervals greater or lesser significance within the resulting average. For example, for a set of 11 intervals, one might average the first 10 intervals, giving the first 4 of these 10 intervals a weight of 0.05 and the remaining six intervals an equal weight of 0.1333. Thus, the invention is not limited to any particular method of averaging or determining a central tendency of the intervals.

Figure 4:
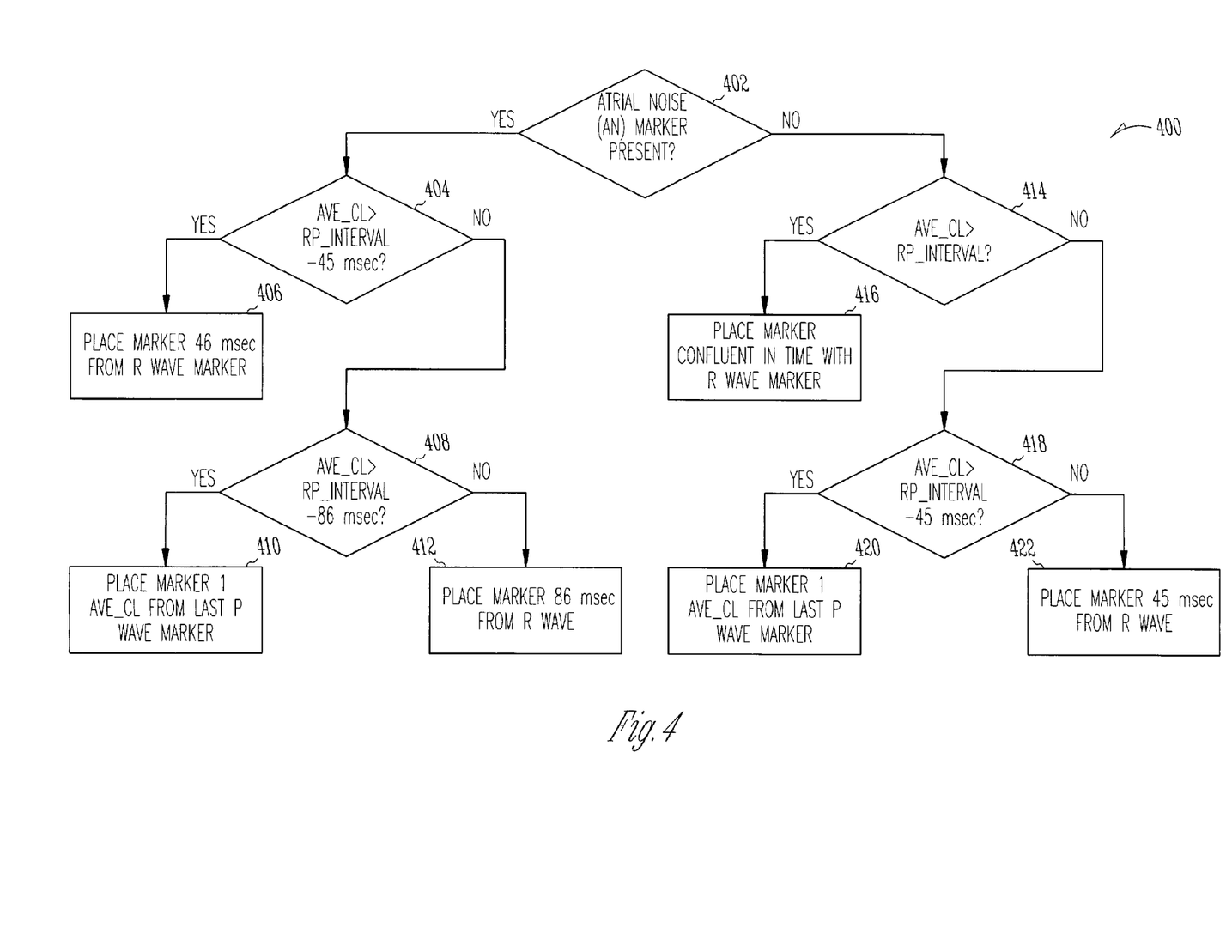
FIG. 4 is a flow chart 400 showing an exemplary implementation of process block 216 in FIG. 2.

After computing the average interval, the processor, at decision block 208, decides if one or more of the intervals has an abnormal length or size relative to other intervals in the set of Y intervals. Generally, this entails determining whether one of the set of intervals has a predetermined size relative one or more of the other intervals. In the exemplary embodiment, this entails determining whether the last, that is, the fourth, of the set of four intervals is 180–220 percent of the average interval. If the fourth interval falls outside this exemplary size range, execution branches to block 210, which is generally representative of any remaining processing desired to continue assessment, or diagnosis, of the rhythmic state corresponding to the current atrial or ventricular intervals. However, if the fourth interval falls inside the exemplary size range, execution branches to decision block 212. The fourth interval 311 in FIG. 4 is 515 milliseconds and thus falls within the exemplary size range.

In decision block 212, the processor decides whether a cardiac event different from those defining the set of Y intervals occurred during the abnormal interval. In the exemplary embodiment, this entails deciding whether a ventricular event occurred during the abnormal atrial interval. If a different cardiac event did not occur during the abnormal interval, the processor branches to block 210 to continue diagnosive processing. On the other hand, if a different cardiac event did occur during the abnormal interval, as shown in FIG. 3 with ventricular event marker 318 and atrial interval 311, the processor branches to decision block 214.

In decision block 214, the processor determines whether the different cardiac event and any concomitant cross-chamber blanking could have prevented lead system 120 from sensing an actual atrial event. To this end, the processor determines whether the different cardiac event, for example, the ventricular event, occurred during a specific portion of the abnormal interval, which the inventor calls the "window of opportunity." FIG. 3 shows that the exemplary embodiment defines the window of opportunity as portion 320a of cross-chamber blanking period 320. Portion 320a ends a predetermined period 320e—for example one average interval period—back from the terminal marker of the abnormal interval (marker 312) and begins a predetermined period 320p—for example 35, 40, 45, 50, 55, or 60 milliseconds—before this point. If the different cardiac event did not occur during this window, the processor branches to block 210 to continue diagnosive processing.

Conversely, if the different cardiac event occurred within this window (320a), the exemplary embodiment branches to block 216 which entails dividing the abnormal interval into at least two new intervals. Some other embodiments disqualify (delete or otherwise omit) the abnormal interval from further processing rather than dividing the interval. FIG. 3 shows that portion 320a of cross-chamber blanking period 320 brackets or overlaps ventricular event marker 318 and thus satisfies this condition. So, for this example, division of the abnormal interval is appropriate.

Dividing the abnormal interval generally entails generating one or more synthetic event markers corresponding to one or more time positions within the abnormal interval, that is, between the beginning and terminal event markers defining the abnormal interval. FIG. 3 shows a synthetic marker 322 placed within portion 320a to divide abnormal interval 311 into two intervals: 311a and 311b which are shown as having different durations. In determining where precisely to place the synthetic marker, the exemplary embodiment follows flow chart 400 in FIG. 4.

Flow chart 400 describes an embodiment which allows for use of atrial and ventricular noise markers and includes blocks 402–412, which, like blocks 202–222 in FIG. 2, are instructive to software, firmware, and hardware implementations. Noise markers indicate that a signal level not immediately classifiable as an event was sensed in the atrial or ventricular channel within a specific window of time, for example, 21, 31, 41, or 51 milliseconds, after a preceding atrial or ventricular sense. In this case, the signal level is assumed to be part of the previous event. In FIG. 3, portion 320b represents a noise window without a noise marker.

Generally, if there is a noise marker, for example an atrial noise marker, within the abnormal interval, the processor places, or defines, the synthetic marker within the noise window, and if there is not a noise marker, the processor places the synthetic marker within the window of opportunity. Exact placement in either window depends on whether the average interval length extended backwards from the terminal marker of the abnormal interval extends past the start of the respective window. If it does, the processor places the synthetic marker at the start of the respective window. If not, the processor determines whether a point placed one average interval back from the terminal marker (marker 312) falls within the respective window. If so, the marker should be placed at the end of one average cycle length from the last atrial marker. If not, the marker should be placed at the end of the respective window.

More precisely, if a noise marker exists within the abnormal interval, the processor branches to block 404 to decide where to put the synthetic marker in the noise window. This entails determining whether a test point which is a predetermined distance, for example the average interval, back from the terminal marker of the abnormal interval lies inside or outside the noise window. This determination is equivalent to asking: Is the average interval (computed at block 206 in FIG. 2) greater than the RP_interval less 45 milliseconds, the length of the blanking period. The RP_interval is defined as the time between the terminal marker for the abnormal interval and the different cardiac event, for example, the time between atrial marker 312 and ventricular marker 318.

If the average interval is greater than this quantity (indicating that the point falls outside the noise window), the processor branches to process block 406, where it places the synthetic marker a predetermined distance, for example, 46 milliseconds, after the marker for the different cardiac event. In this embodiment, placing the synthetic marker 46 milliseconds after the marker for the different cardiac event is equivalent to placing the marker at the start of the noise window.

However, if the average interval is not greater than the abnormal interval less the length of the cross-chamber blanking period, execution continues to decision block 408. In block 408, the processor determines whether the average interval is greater than the RP_interval less some predetermined period, such as 86 milliseconds, the length of the exemplary cross-chamber blanking period. If the average interval is greater than this quantity, the processor branches to block 410, placing the synthetic marker one average interval before the terminal marker of the abnormal interval. On the other hand, if the average interval is less than this quantity, the processor places the synthetic marker a predetermined time, such as 86 milliseconds, after the marker for the different cardiac event, as indicated in process block 412.

If there is no noise marker at decision block 402, the processor determines where within the window of opportunity, for example the cross-chamber blanking period, to place the synthetic marker. The processor places the synthetic marker either coincident with or a certain time after the marker for the different cardiac event.

More particularly, if there is no noise marker, the processor branches to block 414 to determine whether a point measured one average interval back from the terminal marker of the abnormal interval falls inside or outside the window of opportunity. To determine this, the processor decides whether the average interval exceeds the RP_interval. If the average interval exceeds the RP_interval, the processor branches to block 416 where it places the synthetic marker coincident with the marker for the different cardiac event, which also defines the start of the cross-chamber-blanking period. If the average interval does not exceed the RP-interval, the processor branches to decision block 418.

In decision block 418, the processor determines whether a point measured back one average interval from the terminal marker of the abnormal interval falls within the window of opportunity. This entails determining if the average interval is greater than the RP_interval less the length of the window of opportunity, for example, 35, 40, 45, 50, 55, or 60 milliseconds. If the average interval is greater, the processor, at process block 420, places the synthetic marker one average interval before the terminal marker of the abnormal interval. If the average interval is not greater, then the process executes block 422, placing the synthetic marker a predetermined time, such as 35, 40, 45, 50, 55, or 60 milliseconds, after the marker for the different cardiac event.

Some variations of this embodiment use a random or pseudorandom scheme to determine placement of the synthetic marker relative the different cardiac event. For example, the randomly generated time may be generated from a range of 0–5 milliseconds, 0–10 milliseconds, or 10–20 milliseconds relative the different cardiac event. It may also be justifiable to allow placement of a synthetic marker before the different cardiac event, for example, using a randomly generated time from a range of −5 to +5 or −10 to +10 milliseconds relative the different cardiac event. However, in general, it would be improper to place the marker before the beginning of a cross-chamber-blanking period.

After generating the one or more synthetic event markers as shown in FIG. 4, the exemplary embodiment continues to block 220 as shown in FIG. 2. Block 220 entails calculating an average interval based on a set of one or more intervals, including one or more of the new intervals resulting from division of the abnormal interval.

In some embodiments, implantable device 100 includes a wireless transceiver, which permits use of an external programmer to interrogate and program device 100 via bi-directional radio communications. At a minimum, this allows adjustment of one or more of the parameters governing one or more portions of the new methods. For example, one could adjust the number of intervals used in computing the average interval and/or the size threshold for the abnormal interval. These and other parameters can then be set and changed based on observations of a specific patient or group of patients. In other embodiments, the inventor contemplates replacing or supplementing an existing software module or algorithm with one in accord with the present invention.

CONCLUSION

In furtherance of the art, the inventor devised new methods for processing heart electrical signals, some of which ensure accurate interval measurements without unduly delaying therapy decisions or consuming significant battery power. One exemplary method identifies, or detects, an abnormal interval measurement from a set of interval measurements and either disqualifies the abnormal interval from use in making therapy decisions or divides the abnormal interval into two or more other intervals. Ultimately, this and other methods embodying teachings of the present invention, can be incorporated into implantable medical devices, for example, defibrillators, pacemakers, or cardioverter defibrillators, to identify and treat abnormal rhythmic conditions both efficiently and accurately.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A method of processing a first set of one or more intervals corresponding to two or more cardiac events, the method comprising:
   identifying at least one interval based on its size relative to one or more other intervals in the first set of intervals; and
   determining a quantity based on two or more intervals of the first set of intervals other than the identified interval and based on a redefinition of the identified interval as two or more new intervals having at least two different durations.

2. The method of claim 1, wherein determining the quantity based on the two or more intervals other than the identified interval and the redefinition of the identified interval as two or more new intervals comprises determining a central tendency based at least on the two or more intervals and the redefinition of the identified interval.

3. The method of claim 2, wherein determining the quantity comprises calculating an average interval based on the two or more intervals of the set of intervals and at least one of the new intervals.

4. The method of claim 1, wherein determining the quantity based on two or more of the intervals other than the identified interval and the redefinition of the identified interval as two or more new intervals comprises a step for determining a central tendency based at least on the one of the intervals and the redefinition of the identified interval.

5. The method of claim 1:
   wherein identifying the at least one interval based on its size relative to one or more other intervals in the first set of intervals, comprises:
      calculating a set of two or more intervals, with each interval representative of a time between successive cardiac events of a first type; and
   wherein determining the quantity based on two or more intervals of the first set of intervals other than the identified interval and based on a redefinition of the identified interval as two or more new intervals having at least two different durations, comprises:
      identifying an interval based on its size relative to one or more other intervals in the set of intervals;
      determining whether another type of cardiac event, different from the first type, occurred during the identified interval; and
      defining two or more new intervals based on the identified interval.

6. A machine readable medium for use in processing a first set of one or more intervals corresponding to two or more cardiac events, the medium comprising instructions for:

identifying at least one interval based on its size relative to one or more other intervals in the first set of intervals; and determining a quantity based on two or more intervals of the first set of intervals other than the identified interval and based on a redefinition of the identified interval as two or more new intervals having at least two different durations.

7. A method of processing a first set of one or more intervals corresponding to two or more cardiac events, the method comprising:

identifying at least one interval based on its size relative to one or more other intervals in the first set of intervals; and determining a quantity based on at least one of the intervals other than the identified interval and a redefinition of the identified interval as two or more new intervals having at least two different durations.

8. The method of claim 7, wherein determining a quantity based on at least one of the intervals other than the identified interval and a redefinition of the identified interval as two or more new intervals comprises determining a central tendency based at least on the one of the intervals and the redefinition of the identified interval.

9. The method of claim 7 wherein determining the quantity comprises calculating an average interval based on one or more of the intervals of the set of intervals and at least one of the new intervals.

10. The method of claim 7 wherein determining the quantity comprises a step for determining a central tendency based at least on the one of the intervals and the redefinition of the identified interval.

* * * * *